US010639003B2

(12) United States Patent
Takeda et al.

(10) Patent No.: US 10,639,003 B2
(45) Date of Patent: May 5, 2020

(54) ULTRASOUND DIAGNOSIS APPARATUS

(71) Applicant: KONICA MINOLTA, INC., Chiyoda-ku, Tokyo (JP)

(72) Inventors: Yoshihiro Takeda, Hachioji (JP); Kazuya Takagi, Machida (JP); Jo Shikama, Hachioji (JP); Makoto Horiuchi, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 763 days.

(21) Appl. No.: 14/965,887

(22) Filed: Dec. 10, 2015

(65) Prior Publication Data

US 2016/0199024 A1    Jul. 14, 2016

(30) Foreign Application Priority Data

Jan. 9, 2015    (JP) .................. 2015-002780

(51) Int. Cl.
*A61B 8/08* (2006.01)
*A61B 8/00* (2006.01)

(52) U.S. Cl.
CPC .......... *A61B 8/0841* (2013.01); *A61B 8/5215* (2013.01); *A61B 8/4405* (2013.01); *A61B 8/4444* (2013.01)

(58) Field of Classification Search
CPC ... A61B 8/0841; A61B 8/4405; A61B 8/4444; A61B 8/5215
See application file for complete search history.

(56) References Cited

U.S. PATENT DOCUMENTS

2012/0078103 A1* 3/2012 Tashiro ............... A61B 8/0841
600/443

FOREIGN PATENT DOCUMENTS

JP    5473853 B2    4/2014
JP    5486449 B2    5/2014

* cited by examiner

*Primary Examiner* — Christopher L Cook
(74) *Attorney, Agent, or Firm* — Holtz, Holtz & Volek PC

(57) ABSTRACT

An ultrasound diagnosis apparatus generating an ultrasound image of inside of a test object based on ultrasound signals reflected and received from the inside of the test object includes: a candidate region extracting unit which extracts a plurality of candidate detection regions in a needle position range corresponding to a position of a puncture needle inserted into the test object; a needle identification range setting unit which determines a needle identification range including the needle position range from the ultrasound image based on the extracted candidate detection regions; a needle position range estimating unit which determines an estimated range of the needle position range in the needle identification range based on a value indicating an aggregation state related to a distribution of the candidate detection regions in the needle identification range; and a needle emphasizing unit which performs a process for emphasizing the estimated range in the ultrasound image.

8 Claims, 8 Drawing Sheets

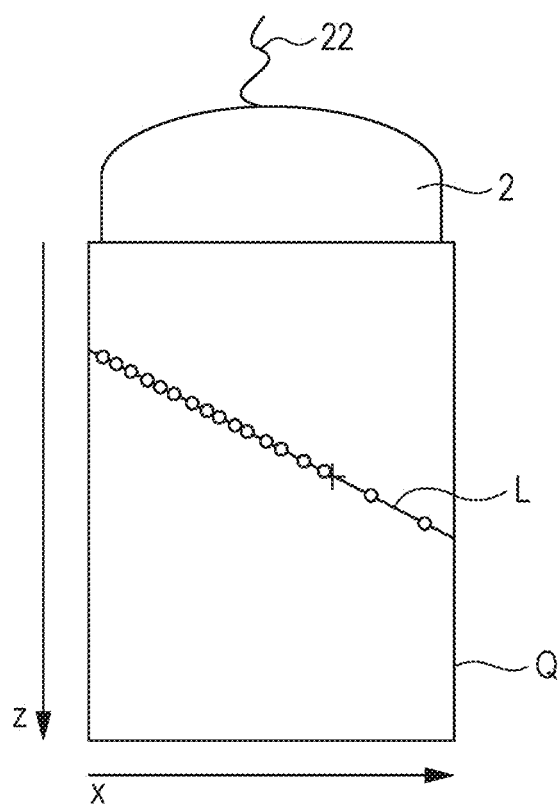

ULTRASOUND DIAGNOSIS APPARATUS

The entire disclosure of Japanese Patent Application No. 2015-002780 filed on Jan. 9, 2015 including description, claims, drawings, and abstract are incorporated herein by reference in its entirety.

BACKGROUND OF THE INVENTION

Field of the Invention

The present invention relates to an ultrasound diagnosis apparatus.

Description of the Related Art

There have been ultrasound diagnosis apparatuses that emit ultrasound waves into a test object, receives waves (echo) reflected from the inside of the test object, and performs predetermined signal data processing, to examine the inner structure of the test object. Such ultrasound diagnosis apparatuses are widely used for various purposes such as medical examinations, treatment, and examinations of the insides of architectural structures.

An ultrasound diagnosis apparatus is used not only to process the data of obtained reflected waves and display an image, but also to collect samples of specific sites (targets) in a test object, release water or the like, or inject and leave a medicinal agent or a marker at a specific site. Such an ultrasound diagnosis apparatus is used in a case where the puncture needle to be used for the above purposes is inserted toward the position of a target while the user is visually checking the puncture needle and the position of the target. With the use of such an ultrasound image, treatment for the target in the test object can be promptly and accurately performed with ease.

However, a puncture needle is normally very thin, and is inserted obliquely into a test object. Therefore, the ultrasound waves that vertically enter the test object are not sufficiently reflected in the transmission/reception direction of the ultrasound waves. Particularly, in the vicinity of the edge of the puncture needle, ultrasound waves are easily scattered. As a result, the puncture needle is not clearly shown in an ultrasound image, and it is difficult: for the user to visually recognize the puncture needle in the ultrasound image.

To counter this problem, various techniques have been developed for enabling users to see a puncture needle more clearly. One of these techniques is a technique of detecting a puncture needle by analyzing an ultrasound image, and emphasizing the puncture needle in the ultrasound image. JP 5473853 B1 discloses a technique of performing a puncture needle emphasizing process by obtaining information about the insertion direction of a puncture needle, and using a filter for emphasizing the edge of the luminance existing in the insertion direction in an ultrasound image. JP 5486449 B1 discloses a technique of identifying the edge of a puncture needle by extracting a high-luminance region in the form of a straight line from an ultrasound image, and identifying the point where the luminance on the straight line becomes higher for the first time from the low-luminance edge side, In a case where the position of the edge of a puncture needle is detected based on the luminance distribution on an identified straight line, however, a completely wrong position is detected as the edge position, if there is noise on the straight line or there is some other structure that reflects ultrasound waves. As a result, the user inappropriately obtains information about the wrong position, and is likely to have a problem. Meanwhile, in a case where the position of the edge of a puncture needle is identified by some other method, the trouble needs to be taken to prepare another structure and perform additional image processing.

SUMMARY OF THE INVENTION

An object of the present invention is to provide an ultrasound diagnosis apparatus that is capable of more appropriately obtaining information about the position of a puncture needle with ease.

To achieve the abovementioned object, according to a first aspect of the invention, an ultrasound diagnosis apparatus generating an ultrasound image of the inside of a test object based on ultrasound signals reflected and received from the inside of the test object, the ultrasound diagnosis apparatus reflecting one aspect of the present invention comprises: a candidate region extracting unit that extracts candidate detection regions in the needle position range corresponding to the position of a puncture needle inserted into the test object; a needle identification range setting unit that determines a needle identification range including the needle position range from the ultrasound image based on the extracted candidate detection regions; a needle position range estimating unit that determines an estimated range of the needle position range in the needle identification range based on the value indicating the aggregation state related to the distribution of the candidate detection regions in the needle identification range; and a needle emphasizing unit that performs a process for emphasizing the estimated range in the ultrasound image.

Further, according to a second aspect of the invention, in the ultrasound diagnosis apparatus of the first aspect, the value indicating the aggregation state preferably includes the number of the candidate detection regions existing in the needle identification range, and the estimated range is preferably determined in accordance with the number of the candidate detection regions.

Further, according to a third aspect of the invention, in the ultrasound diagnosis apparatus of the first aspect, the value indicating the aggregation state preferably includes variance among the positions of the respective candidate detection regions in the aggregation of the candidate detection regions existing in the needle identification range, and the estimated range is preferably determined in accordance with the variance.

Further, according to a fourth aspect of the invention, in the ultrasound diagnosis apparatus of any one of the first to third aspects, the needle emphasizing unit preferably performs weighting on a result of estimate of the estimated range in each region dividing the estimated range based on the value indicating the aggregation state, and performs a process for emphasizing the inside of the estimated range with the degree of emphasis corresponding to the weighting.

Further, according to a fifth aspect of the invention, in the ultrasound diagnosis apparatus of the fourth aspect, the value indicating the aggregation state preferably includes a value that is set as the center position in the aggregation of the candidate detection regions existing in the needle identification range, and the needle emphasizing unit preferably performs the weighting, using a predetermined window function to reduce the weight at least on one side of the center position.

Further, according to a sixth aspect of the invention, in the ultrasound diagnosis apparatus of the fifth aspect, the value indicating the aggregation state preferably includes variance among the positions of the respective candidate detection regions in the aggregation of the candidate detection regions existing in the needle identification range, the estimated range is preferably determined in accordance with the variance, and the variance is preferably determined independently on either side of the center position.

Further, according to a seventh aspect of the invention, in the ultrasound diagnosis apparatus of fifth or sixth aspect, the center position is preferably a weighted average position in the aggregation of the candidate detection regions existing in the needle identification range.

Further, according to an eighth aspect of the invention, in the ultrasound diagnosis apparatus of seventh aspect, the weighted average position is preferably a position calculated in accordance with the distribution of the candidate detection regions weighted with the values corresponding to the intensities of the ultrasound signals in the candidate detection regions existing in the needle identification range.

Further, according to a ninth aspect of the invention, in the ultrasound diagnosis apparatus of any one of the first to eighth aspects, the candidate region extracting unit preferably extracts the candidate detection regions based on the distribution of the ultrasound signals in the incident direction of ultrasound waves entering the test object.

Further, according to a tenth aspect of the invention, in the ultrasound diagnosis apparatus of any one of the first to ninth aspects, the needle identification range setting unit preferably sets the needle identification on range in the form of a straight line having neither end determined in the ultrasound image.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 6 is a diagram for explaining a puncture needle emphasizing process;

DESCRIPTION OF THE PREFERRED EMBODIMENTS

Figure 1:
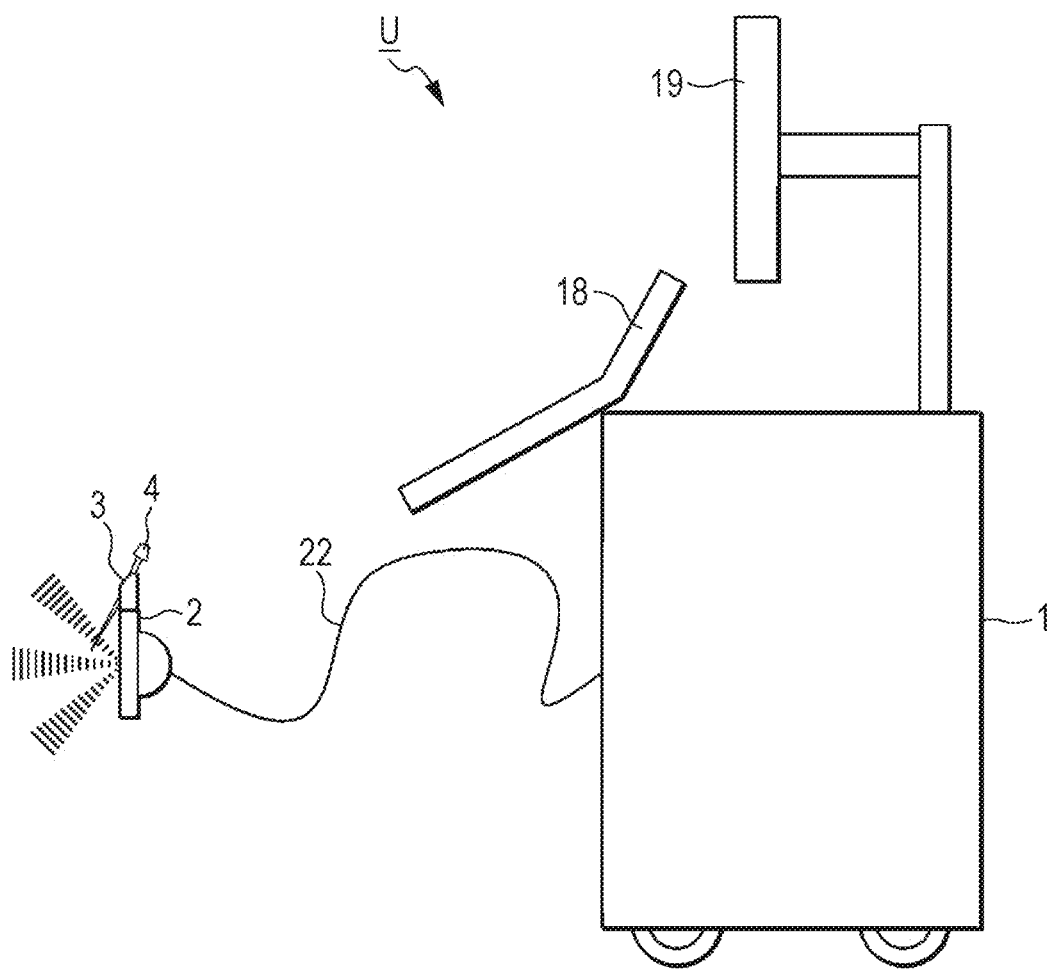
FIG. 1 is a diagram showing the entire structure of an ultrasound diagnosis apparatus according to an embodiment of the present invention.
Figure 2:
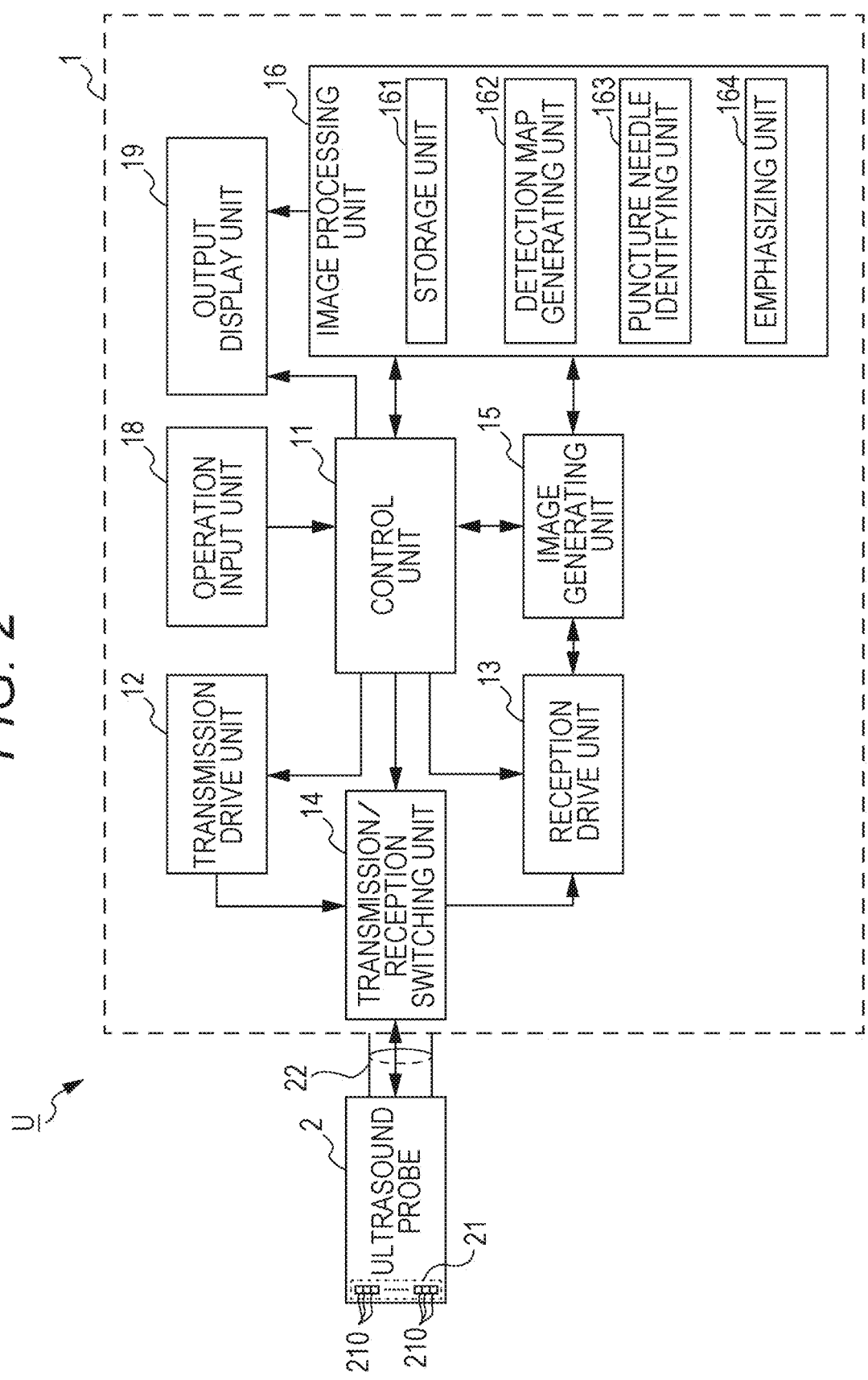
FIG. 2 is a block diagram showing the inner structure of the ultrasound diagnosis apparatus.

Hereinafter, an embodiment of the present invention will be described with reference to the drawings. However, the scope of the invention is not limited to the illustrated examples. FIG. 1 is a diagram showing the entire structure of an ultrasound diagnosis apparatus U according to this embodiment. FIG. 2 is a block diagram showing the inner structure of the ultrasound diagnosis apparatus U.

As shown in FIG. 1, this ultrasound diagnosis apparatus U includes an ultrasound diagnosis apparatus main frame 1, an ultrasound probe 2 (a transmitting/receiving unit) connected to the ultrasound diagnosis apparatus main frame 1 via a cable 22, an attachment unit 4 (an attachment or an insertion mechanism) attached to the ultrasound probe 2, a puncture needle 3, and the like.

In this case, the puncture needle 3 has the form of a hollow long needle, and is inserted into a test object at an angle predetermined in accordance with the settings of the attachment unit 4. The puncture needle 3 can be replaced with one having an appropriate thickness, an appropriate length, and an edge in an appropriate shape in accordance with the type and the amount of the target (specimen) to be obtained or the medicine to be injected.

The attachment unit 4 holds the puncture needle 3 oriented in a predetermined direction. The attachment unit 4 is attached to a side of the ultrasound probe 2, and can appropriately change the orientation of the puncture needle 3 in accordance with the insertion angle of the puncture needle 3 with respect to the test object. Instead of the attachment unit 4, a guide unit that holds the puncture needle 3 oriented in the insertion direction may be provided directly on the ultrasound probe 2.

An operation input unit 18 and an output display unit 19 are provided on the ultrasound diagnosis apparatus main frame 1. As shown in FIG. 2, the ultrasound diagnosis apparatus main frame 1 also includes a control unit 11, a transmission drive unit 12, a reception drive unit 13, a transmission/reception switching unit 14, an image generating unit 15, an image processing unit 16, and the like.

Based on an operating signal generated by an input operation performed from outside through an input device such as the keyboard or the mouse of the operation input unit 18, and on a detection signal from a touch sensor that detects a touch operation performed on the display screen, the control unit 11 of the ultrasound diagnosis apparatus main frame 1 outputs a drive signal to the ultrasound probe 2 and causes the ultrasound probe 2 to output ultrasound waves. The control unit 11 also performs various processes by obtaining reception signals related, to ultrasound reception from the ultrasound probe 2. By doing so, the control unit 11 performs a series of operations to display results and the like on the display screen of the output display unit 19 as necessary.

The control unit 11 includes a CPU (Central Processing Unit), an HDD (Hard Disk Drive), and a RAM (Random Access Memory), and the like. The CPU reads various kinds of programs stored in the HDD, loads the programs into the RAM, and collectively controls operations of the respective components of the ultrasound diagnosis apparatus U in accordance with the programs. The HDD stores the control program and various processing programs for operating the ultrasound diagnosis apparatus U, various kinds of setting data, and the like. These programs and setting data may not only be stored in the HDD but also be rewritably stored in an auxiliary storage device using a nonvolatile memory such as a flash memory including an SSD (Solid State Drive). The RAM is a volatile memory such as an SPAN or a DRAM, provides a work memory space for the CPU, and temporarily stores data.

The transmission drive unit 12 outputs a pulse signal to be supplied to the ultrasound probe 2 in accordance with a control signal that is input from the control unit 11, and causes the ultrasound probe 2 to generate ultrasound waves. The transmission drive unit 12 includes a clock generation circuit, a pulse generation circuit, a pulse width setting unit, and a delay circuit, for example. The clock generation circuit is the circuit that generates clock signals that determine the timing to transmit a pulse signal and the transmission frequency. The pulse width setting unit sets the waveform (shape), the voltage amplitude, and the pulse width of the transmission pulse to be output from the pulse generation circuit. The pulse generation circuit generates the transmission pulse based on the settings of the pulse width setting unit, and outputs the transmission pulse to wiring paths that are different among the respective oscillators 210 of the ultrasound probe 2. The delay circuit counts clock signals that are output from the clock generation circuit. When a predetermined delay time has passed, the delay circuit causes the pulse generation circuit to generate the transmission pulse and output the transmission pulse to the respective wiring paths.

The reception drive unit 13 is the circuit that obtains a reception signal input from the ultrasound probe 2, under the control of the control unit 11. The reception drive unit 13 includes an amplifier, an A/D converter circuit, and a phasing adder circuit, for example. The amplifier is the circuit that amplifies reception signals corresponding to ultrasound waves received by the respective oscillators 210 of the ultrasound probe 2, at a predetermined amplification factor. The A/D converter circuit is the circuit that converts the amplified reception signals into digital data at a predetermined sampling frequency. The phasing adder circuit is the circuit that adjusts the time phase by providing a delay time to each of the reception signals subjected to the A/D conversion in the respective wiring paths corresponding to the oscillators 210, and generates sound-ray data by adding up the adjusted reception signals (phasing addition).

Under the control of the control unit 11, the transmission/reception switching unit 14 causes the transmission drive unit 12 to transmit a drive signal to the oscillators 210 when ultrasound waves are emitted (transmitted) from the oscillators 210, and performs a switching operation to cause the reception drive unit 13 to output a reception signal when obtaining signals related to ultrasound waves emitted from the oscillators 210.

The image generating unit 15 generates a diagnostic image (ultrasound image) based on received data (ultrasound signals) of ultrasound waves. The image generating unit 15 obtains signals by detecting sound-ray data input from the reception drive unit 13 (envelope detection), and performs logarithm amplification, filtering (such as low-pass filtering or smoothing), an emphasizing process, or the like, as necessary. The image generating unit 15 generates, as a diagnostic image, frame image data related to B-mode display showing a two-dimensional structure (the structure in the test object) in a plane including the direction of transmission of a signal as a luminance signal in accordance with the signal intensity (the incident direction or the depth direction of the test object) and the scan direction of ultrasound waves transmitted from the ultrasound probe 2. At this point, the image generating unit 15 can adjust the dynamic range related to the display, or perform gamma correction, for example. This image generating unit 15 may include a CPU and a RAM exclusively used for generating those images. In the image generating unit 15, a hardware structure exclusively for image generation may be formed on a circuit board (such as an ASIC (Application—Specific Integrated Circuit)). Alternatively, the process related to image generation may be performed by the CPU and the RAM of the control unit 11 for the image generating unit 15.

The image processing unit 16 detects the puncture needle 3 from a generated diagnostic image, performs various processes for conducting emphasized display, and temporarily stores the detected image until the timing of display. The image processing unit 16 includes a storage unit 161, a detection map generating unit 162 (a candidate region extracting unit), a puncture needle identifying unit 163 (a needle identification range setting unit), an emphasizing unit. 164 (a needle position range estimating unit or a needle emphasizing unit), and the like.

The storage unit 161 stores each frame of diagnostic image data (frame image data) that has been processed by the image generating unit 15 and is used in realtime display or display similar to realtime display. The diagnostic image data stored in the storage unit 161 is of a predetermined number of most recent frames. The storage unit 161 is a volatile memory such as a DRAM (Dynamic Random Access Memory). Alternatively, the storage unit 161 may be a nonvolatile memory that can be rewritten at high speed. The diagnostic image data stored in the storage unit 161 is read under the control of the control unit 11, and is then transmitted to the output display unit 19 or is output to the outside of the ultrasound diagnosis apparatus U via a communication unit not shown in the drawing. If the display method of the output display unit 19 is a television method, a DSC (Digital Signal Converter) is provided between the storage unit 161 and the output display unit 19, and the diagnostic image data may be output after conversion of the scan format. The storage unit 161 can also store diagnostic image data required to be stored in accordance with an operation that is input to the operation input unit 18 by the user of the ultrasound diagnosis apparatus U, for a predetermined period during operation of the ultrasound diagnosis apparatus U or until the diagnostic image data is erased in accordance with an input operation of the user.

The detection map generating unit 162 generates detection map data for the puncture needle identifying unit 163 to identify the puncture needle 3. The detection map data will be described later in detail.

The puncture needle identifying unit 163 identifies the puncture needle 3, using the detection map data generated by the detection map generating unit 162. The puncture needle identifying unit 163 stores the history of positions of the puncture needle detected so far, and can calculate the rate of change in the position and the direction of change (shift vector), for example. In this case, the puncture needle identifying unit 163 can estimate the next position of the puncture needle 3 based on the detected positions of the puncture needle 3 and the shift vector, and use the estimated next position at the time of identification.

The emphasizing unit 164 performs the process for emphasizing the position of the identified puncture needle 3 in a diagnostic image. The emphasizing unit 164 determines the contents of the emphasizing process in accordance with the position of the puncture needle 3 identified by the puncture needle identifying unit 163 and the identification accuracy, performs the emphasizing process on a diagnostic image, and stores the diagnostic image into the storage unit 161.

The detection map generating unit 162, the puncture needle identifying unit 163, and the emphasizing unit 164 may share the CPU and the RAM of the image processing unit 16, or may each include a CPU and a RAM. Alternatively, the various kinds of processes may be performed by the CPU and the RAM of the control unit 11 for the detection map generating unit 162, the puncture needle identifying unit 163, and the emphasizing unit 164.

The operation input unit 18 includes a push-button switch, a keyboard, a mouse, a trackball, or a touch sensor for the display screen, or includes a combination of them. The operation input unit 18 converts a user input operation into an operating signal, and inputs the operating signal into the ultrasound diagnosis apparatus main frame 1.

The output display unit 19 includes a display screen that uses one of various display methods such as LCD (Liquid Crystal Display), organic EL (Electro-Luminescent) display, inorganic EL display, plasma display, and CRT (Cathode Ray Tune) display. The output display unit 19 also includes a drive unit for the display screen. The output display unit 19 generates a drive signal for the display screen (various display pixels) in accordance with a control signal output from the control unit 11 and image data generated by the image processing unit 16. The output display unit 19 displays, on the display screen, a menu and a status related to an ultrasound diagnosis, and measurement data based on received ultrasound waves. The output display unit 19 may also include an LED map or the like, and display that the power is on or off.

The operation input unit 18 and the output display unit 19 may be integrally formed with the housing of the ultrasound diagnosis apparatus main frame 1, or may be attached to the outside via RGB cables, USB cables, HDMI (a registered trade name) cables, or the like. If an operation input terminal or a display output terminal are provided in the ultrasound diagnosis apparatus main frame 1, conventional peripheral devices for operation and display may be connected to those terminals and be used.

The ultrasound probe 2 generates ultrasound waves (at approximately 1 to 30 MHz in this example) and emits the ultrasound waves to the test object such as a living body. The ultrasound probe 2 also functions as an acoustic sensor that receives the emitted ultrasound waves reflected from the test object (echo) and converts the reflected waves into electrical signals. This ultrasound probe 2 includes an oscillator array 21 of the oscillators 210 that transmit and receive ultrasound waves, and the cable 22.

A connector (not shown) to be connected to the ultrasound diagnosis apparatus main frame 1 is provided at one end of the cable 22, and the ultrasound probe 2 can be detachably attached to the ultrasound diagnosis apparatus main frame 1 by virtue of the cable 22. A user operates the ultrasound diagnosis apparatus U by brining the ultrasound wave transmission/reception surface of the ultrasound probe 2, or the surface from which ultrasound waves from the oscillator array 21 are emitted, into contact with the test object with a predetermined pressure. By doing so, the user conducts ultrasound diagnosis.

It should be rioted that the ultrasound diagnosis apparatus main frame 1 and the ultrasound probe 2 can be connected by a wireless communication means such as infrared rays or radio waves, instead of the cable 22.

The oscillator array 21 is an array of the oscillators 210 each formed with a piezoelectric element including a piezoelectric body and electrodes that are provided at both ends of the piezoelectric body and have charges appearing when the piezoelectric body is deformed (expanded or contracted). For example, the oscillator array 21 is a one-dimensional array extending in a predetermined direction (the scan direction). The piezoelectric bodies are deformed in accordance with the electrical fields generated therein as a voltage pulse (a pulse signal) is sequentially supplied to the oscillators 210. As a result, ultrasound waves are generated. Further, as ultrasound waves in a predetermined frequency band are emitted to the oscillators 210, the thickness of each piezoelectric body varies (vibrates) due to the sound pressure, and the charge corresponding to the variation is generated. The amount of the charge is then converted into an electrical signal, and is output.

Next, a method of detecting the puncture needle 3 in the ultrasound diagnosis apparatus U of this embodiment is described in detail.

Figure 3:
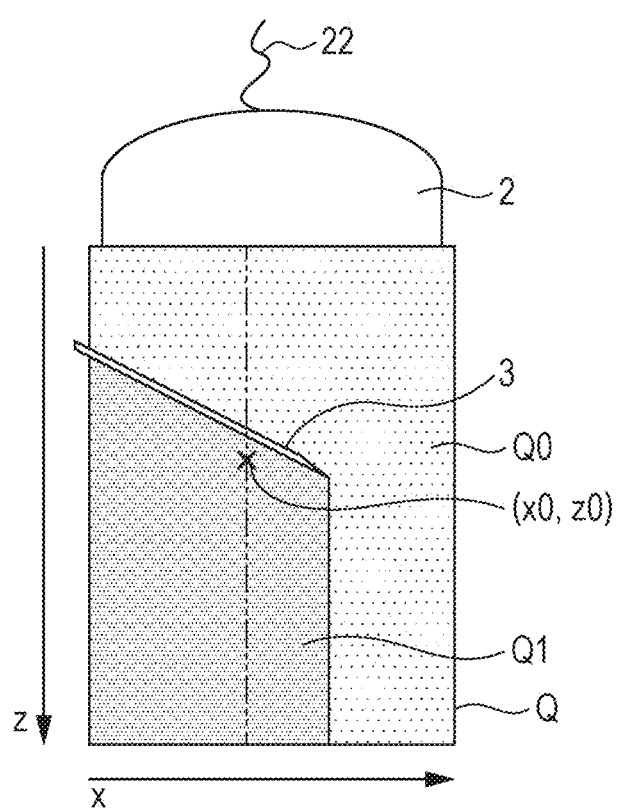
FIG. 3 is a schematic diagram for explaining calculation of detection map data related to puncture needle detection.
Figure 4A:
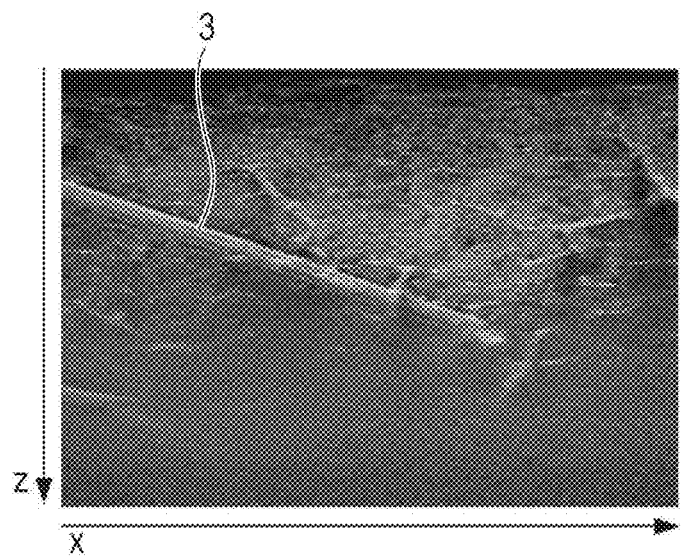
FIGS. 4A to 4C are diagrams showing an example of calculation of puncture needle detection map data.
Figure 4B:
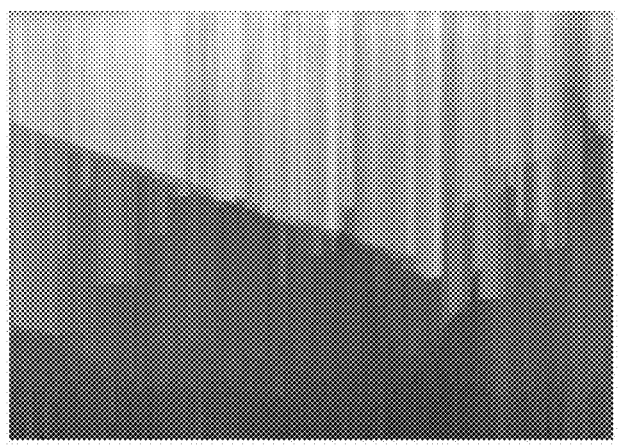
Figure 4C:

FIG. 3 is a schematic diagram for explaining calculation of detection map data related to puncture needle detection. FIGS. 4A to 4C are diagrams showing an example of calculation of puncture needle detection map data.

In this example, ultrasound waves enter the ultrasound probe 2 shown on the upper side of the drawing and travel downward (in the z-direction). The ultrasound waves are then reflected inside a test object Q, and the reflected waves travel upward and are then received and detected.

The puncture needle 3 has a large ultrasound component to be reflected in a different direction (an obliquely upward direction in FIG. 3) from the vertically upward direction depending on the thickness and the tilt thereof, and has a small component that continues to propagate downward. As a result, the region Q1 below the puncture needle 3 serves as an ultrasound shadow region (an acoustic shadow), and the ultrasound component reflected in the region Q1 becomes smaller than that in the other region Q0 in total. Therefore, the ultrasound diagnosis apparatus U of this embodiment detects the puncture needle 3 by identifying the boundary between the region Q0 and the region Q1.

If ultrasound waves propagate to both sides of the puncture needle 3 (in a direction perpendicular to the display surface (back and forth) in FIG. 3) at this point, the decrease in the intensity of the lower reflected waves becomes relatively smaller. Therefore, the transmission/reception width of ultrasound waves is preferably not too greater than the width of the puncture needle 3.

So as to identify this boundary, analysis is first conducted based on a distribution of luminance values in the incident direction (z-direction) of ultrasound waves incident on each pixel position with respect to the luminance value s (x0, z0) (x0 and z0 being integers not smaller than 0) in accordance with the reflected wave intensity at each pixel position (represented by the coordinates (x0, z0) at an upper left portion in the rectangular region in this case). Here, an average value $sa=\Sigma s(x\ 0,\ z \le z0)/(z0+1)$ is calculated as a characteristic value of the reflected wave intensity obtained at each pixel position on the shallower side ($z \le z0$) of the test object Q than the pixel position (x0, z0). This average value sa temporarily increases as the proportion of the high-luminance region becomes larger at each pixel position on the shallower side (the side on which z is smaller) than the above mentioned boundary position. At each pixel position on the deeper side (the side on which z is greater), the average value sa becomes gradually smaller as the proportion of the low-luminance region becomes larger. At positions where the puncture needle 3 is not inserted, the entire density does not drop, and therefore, the average value sa does not greatly vary.

Meanwhile, at each pixel position (x0, z0), a maximum value $sm=\max(s(x0,\ z \ge z0)$ is calculated as a characteristic value of the reflected wave intensity obtained at each pixel position on the deeper side ($z \ge z0$) of the test object Q than the pixel position. If a high-luminance point exists at a shallow position in the test object Q this maximum value sm discontinuously decreases as the coordinate z0 in the depth direction becomes greater, with the high-luminance point being the boundary. There is a high possibility that this discontinuous decrease continues at the position of the puncture needle 3.

Accordingly, at each pixel position (x0, z0), a feature amount sc=sa−sm, which is the difference between the average value sa and the maximum value sm, becomes larger, when sa becomes larger and sm becomes smaller at the position of the puncture needle 3. Further, the partial differential value of this feature amount sc in the z-direction (the difference value from an adjacent pixel position) ds (x0, z0)=∂s/∂z, or simply sc (x0, 0)−sc (x0, z0−1), is calculated with respect to each set of x0 and z0, to obtain detection map data.

The two-dimensional map of this feature amount sc to be obtained with respect to the diagnostic image shown in FIG. 4A is shown in FIG. 4B, and the detection map data to be obtained is shown in FIG. 4C.

After the partial differential values ds are obtained with respect to all the pixel positions, detection of the puncture needle 3 is conducted with this detection map data. In this detection, a conventional sensing method, or more particularly, a method of detecting a straight line from image data is used. In this case, Hough transform is used, for example.

FIGS. 5A to 5D are diagrams showing an example of detection of the straight line corresponding to the puncture needle 3 based on the detection map data obtained in FIG. 4C.

Figure 5A:
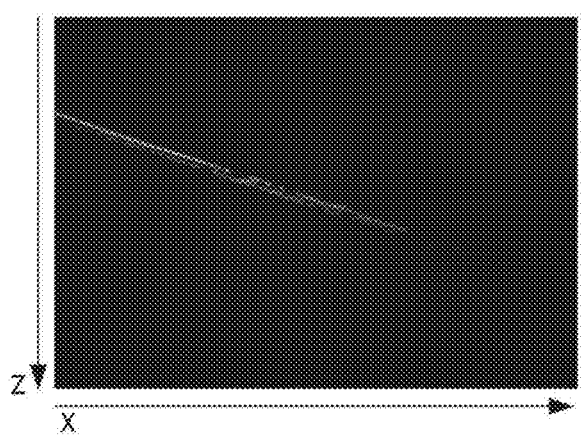
FIGS. 5A to 5D are diagrams showing an example of detection of the straight line corresponding to the puncture needle based on the detection map data.
Figure 5B:
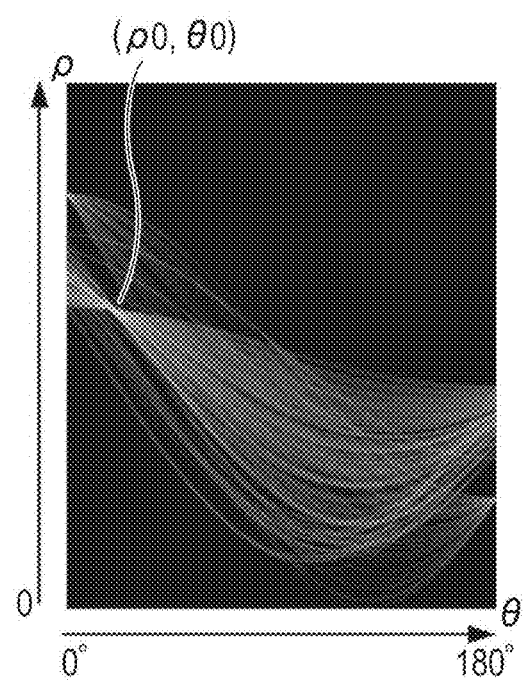

The partial differential values ds that are the values at the respective points in the detection map data obtained in FIG. 4C are binarized with a predetermined threshold value, for example, and the points equal to or higher than the threshold value are set as candidate points (xi, zi) for the puncture needle 3 (a distribution of candidate detection regions), as shown in FIG. 5A. The candidate points (xi, zi) normally fail to clarify the range (the needle position range) corresponding to the position of the entire puncture needle 3 in the ultrasound image, and are often defined discretely.

Figure 5C:
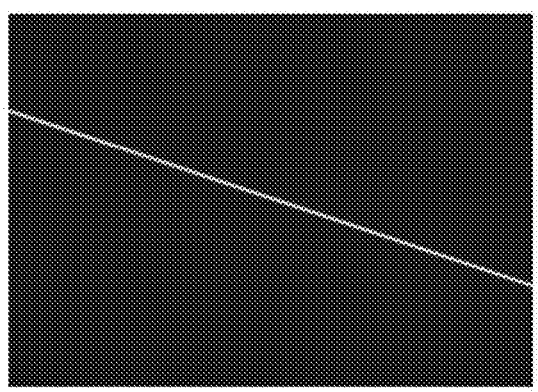

Since the puncture needle 3 normally has the shape of a straight line, detection of the same straight line as the shape of the puncture needle 3 on which the candidate points concentrate is conducted through Hough transform (FIG. 5B) Where each candidate point (xi, zi) is expressed as ρ=xi·cos θ+zi·sin θ, in which ρ represents a length variable and θ represents an angular variable, ρ and θ satisfying the expression represent the length of the perpendicular from the origin to the straight line passing through the candidate points (xi, zi), and the angle between the x-axis and the straight line, respectively. Accordingly, the point (ρ0,θ0) to which the largest number of candidate points (xi, zi) extend represent the likeliest straight line (candidate line) to pass through those candidate points (FIG. 5C).

As a method of detecting a line segment, instead of a straight line, there is probabilistic Hough transform. In this probabilistic Hough transform, a candidate line is detected from randomly selected points through Hough transform, and the existence range of the selected points on the candidate line is checked. Through this process, the start point and the end point of the candidate line are determined. As a result, a line segment (a length) can be detected.

In a case where there are candidate points aligned in a straight line other than the puncture needle 3, it is not necessary to narrow down to one candidate line, and there may be two or more candidate lines. Further, in a case where the position of the puncture needle 3 can be estimated beforehand by some other method, a candidate line for the puncture needle 3 may be selected from among candidate lines based on the estimate. The puncture needle 3 (the needle position range) exists at least in a portion of the candidate line (the needle identification range) selected in the above manner.

Figure 5D:
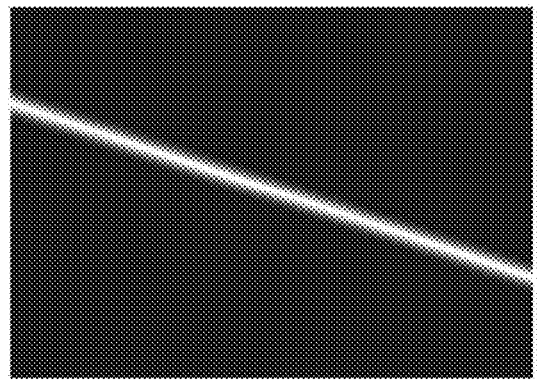

After the candidate line is detected, the degree of emphasis of the candidate line is determined in accordance with the accuracy of the candidate line (FIG. 5D). That is, even in a case where there still remain two or more candidate lines, the degrees of emphasis can be made to vary between a candidate line with a high possibility of corresponding to the puncture needle 3 and a candidate line with a low possibility of corresponding to the puncture needle 3.

Next, emphasized display of the puncture needle 3 in a diagnostic image is described.

In the ultrasound diagnosis apparatus U of this embodiment, emphasized display of the puncture needle 3 is performed by superimposing emphasized display of a range (an estimated range) in which the puncture needle 3 on a candidate line selected in a diagnostic image is most likely to exist on the diagnostic image with the degree of emphasis corresponding to the likelihood of existence of the puncture needle 3.

FIG. 6 is a diagram for explaining the emphasizing process for the puncture needle 3.

Since either end is not determined for a candidate line L selected through Hough transform as described above, the edge position of the puncture needle 3 cannot be identified simply with the candidate line L. Further, the edge portion of the puncture needle 3 has more ultrasound wave scattering than at the other portions of the puncture needle 3 due to its shape or the like, and has even fewer reflected waves. Therefore, it is difficult to identify the edge portion of the puncture needle 3 in some cases. If there is noise or an ultrasound wave reflecting structure in front of the edge portion, the position of the noise or the structure is wrongly recognized as the position of the edge, and a range that is not the correct range might be emphasized on display. Therefore, in the ultrasound diagnosis apparatus U of this embodiment, the likeliest range of the puncture needle 3 is estimated based on parameters possibly related to the needle position range, such as values (the center position in the aggregation and the degree of aggregation, for example) indicating the aggregation state related to the distribution of the candidate points used in selecting the candidate line L. Weights for the respective pixels (regions) in this estimated range are then set, and this estimated range is emphasized and displayed (restricted emphasis).

In the diagram in FIG. 6, more candidate points schematically indicated by circles (o) are distributed at the left side on the candidate line L. In the vicinity of the position of the actual edge of the puncture needle 3 marked with a positive sign (+), fewer candidate points exist than in the vicinity of the left edge, and there exist some candidate points beyond (on the right side of) the edge position.

In this example, all the candidate points (xi, zi) (1≤i≤N) on the candidate line are first weighted with the feature amounts ωi=sc (xi, zi) at the respective candidate points (xi, zi), respectively. In this manner, a weighted average position (xc, zc) is calculated. Specifically, the weighted average position (xc, zc) is calculated according to xc=Σ(ωi·xi)/Σ(ωi) and zc=Σ(ωi·zi)/Σ(ωi), using N candidate points (xi, zi) and N feature amounts ωi, which satisfy 1≤i≤N. With the weighted average position (xc, zc) serving as the reference (the center position), the degree of emphasis is lowered with a predetermined filter (a window function). Although not particularly limited, the filter is a window function such as a Gaussian window or a Hamming window, and the width of the window (applied width) is determined by the variance (standard deviation) of the candidate points or simply by the number of the candidate points, for example. Alternatively, depending on circumstances, the length of a candidate line in the diagnostic image may be used as the width of the window, regardless of the actual distribution of the candidate points. If there is no need to lower the degree of emphasis in the estimated range in accordance with the usage state or the liking of the user, a rectangular window may be used. The variance may be separately calculated on the left side and the right, side of the weighted average position, or a degree of distortion and a kurtosis, as well as the variance, may be calculated and used. These window functions may be appropriately selected from lists in accordance with the number and the distribution of the candidate points.

In this case, a narrow weighting range is uniquely set or is set in accordance with the importance of the usage of the puncture needle 3 and the information about the edge position, and only the center portion in which the puncture needle 3 certainly exists is mainly emphasized. Alternatively, a wide weighting range is set, so that a range that has a low possibility of existence of the puncture needle 3 but is beyond the predetermined reference level is emphasized so as to be visually recognized by the user with ease.

Further, so as to adjust the degree of emphasis to the range of existence of the puncture needle 3, the density of candidate points may be calculated in each range of a predetermined size, and the degree of emphasis is not lowered in each range having a density equal to or higher than a predetermined ratio to the density in the range including the weighted average position. Particularly, in a case where the puncture needle 3 crosses one end of the diagnostic image including the puncture needle 3, the degree of emphasis of the puncture needle 3 between the weighted average position and the end may not be restricted. Alternatively, since the number of candidate points on the candidate line L normally becomes larger as the range of existence of the puncture needle 3 becomes longer, a range in which the degree of emphasis is not to be lowered may be set or the window width of the filter may be changed in accordance with the number of candidate points.

Further, the position of the edge of the puncture needle 3 may be estimated by some other method in a range in which the processing does not become complicated, and a window width may be set in accordance with the distance between the weighted average position and the position of the edge of the puncture needle 3.

Figure 7A:
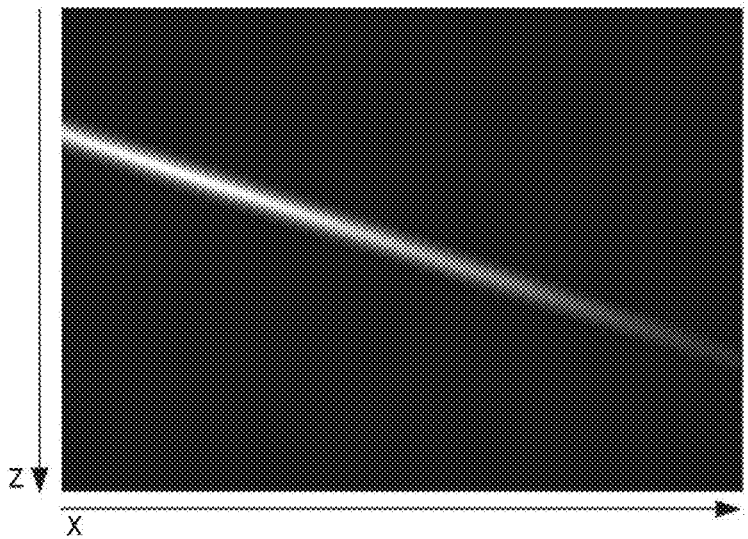
FIGS. 7A and 7B are diagrams showing an example of emphasized display of an identified puncture needle position.
Figure 7B:
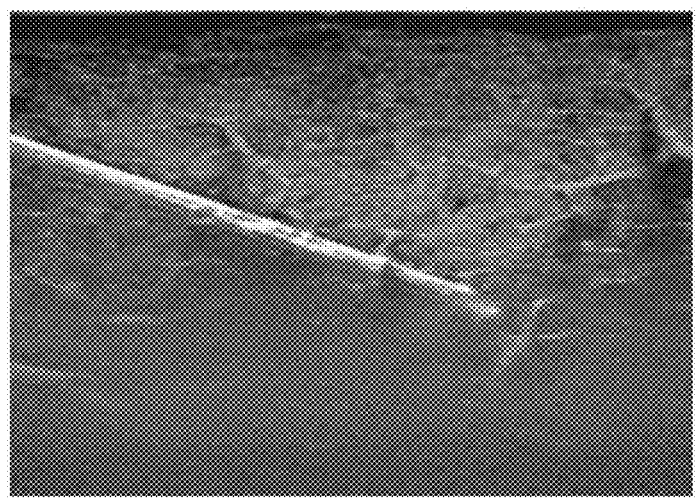

FIGS. 7A and 7B are diagrams showing an example of emphasized display of the position of the puncture needle 3 identified by the ultrasound diagnosis apparatus U of this embodiment.

The degree of emphasis determined in FIG. 5D is restricted in accordance with the distribution (aggregation state) of the candidate points on the candidate line L as described above, and the degree of display emphasis is lowered at the right side in the diagnostic image as shown in FIG. 7A. This emphasized display is superimposed on the original diagnostic image, so that an output image (FIG. 7B) is generated. This emphasized display is colored in a different tone (blue, for example) from the color tone of the original diagnostic image (monochrome display, for example).

Figure 8:
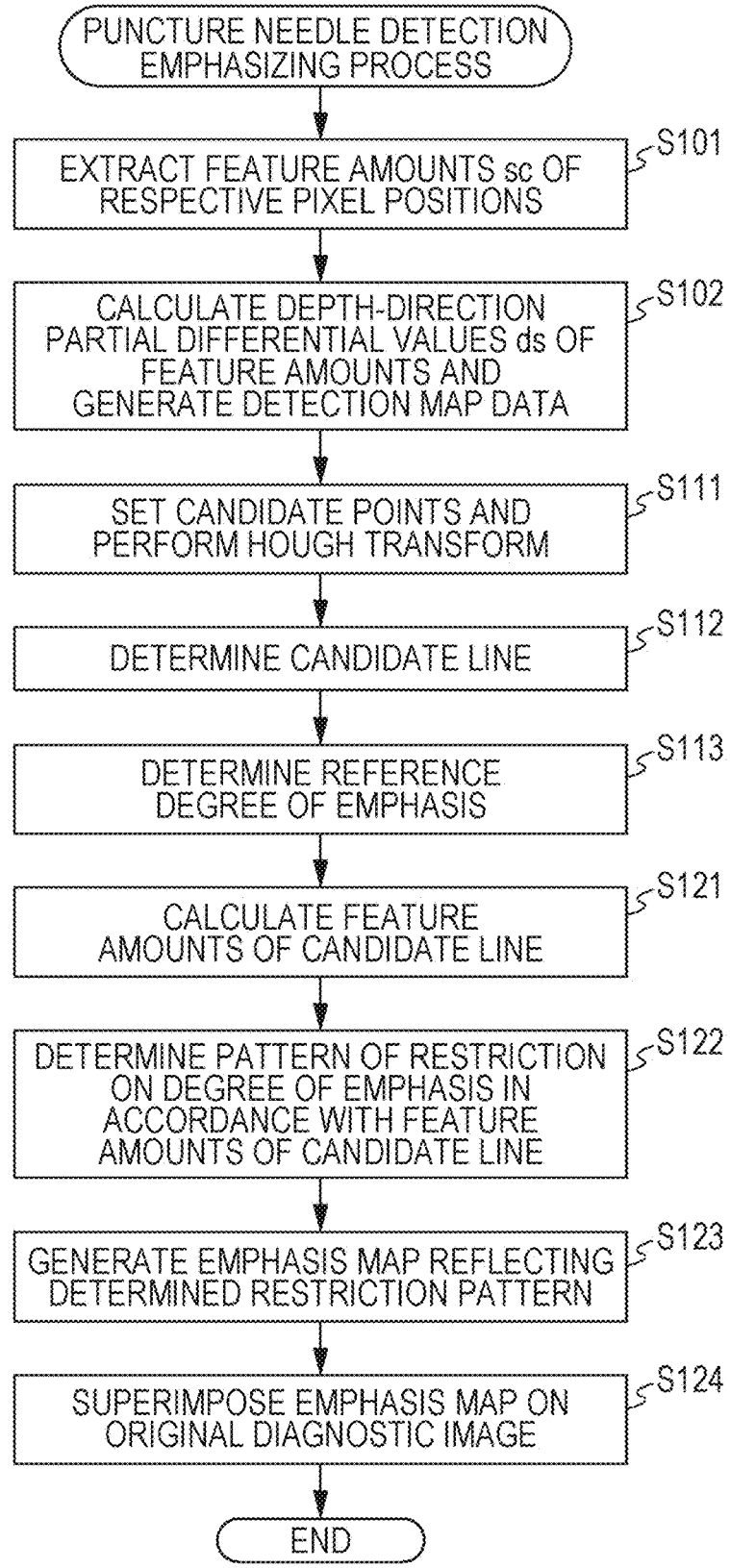
FIG. 8 is a flowchart showing the control procedures in a puncture needle detection emphasizing process.

FIG. 8 is a flowchart showing the control procedures in a puncture needle detection emphasizing process in the ultrasound diagnosis apparatus U of this embodiment.

This process is performed by the CPU of the control unit 11 or the image processing unit 16 as described above, When the puncture needle detection emphasizing process starts, the CPU, using the detection map generating unit 162, calculates the feature amounts sc at the respective pixel positions from a two-dimensional structure image (a diagnostic image) of a test object in the same manner as in the conventional B-mode, and stores the feature amounts sc associated with pixel position information (step S101). The CPU further processes the feature amounts sc to obtain partial differential values ds, and generates the map data for detecting the puncture needle 3 (step S102). The CPU compares the respective values in the detection map data with a predetermined reference value, to extract the candidate points in the range of the puncture needle 3.

Using the puncture needle identifying unit 163, the CPU performs Hough transform on the extracted candidate points, and detects a straight line (step S111) From the detected straight line, the CPU determines a candidate line as a candidate for the puncture needle 3 (step S112). The CPU determines the reference degree of emphasis for emphasizing the display of the candidate line (step S113)

Using the emphasizing unit. 164, the CPU calculates the parameters related to the position and the range of emphasized display and the distribution of the degree of emphasis (step S121). The CPU determines the weight setting (the restriction pattern) of the emphasis range in accordance with the likelihood of being the range corresponding to the puncture needle 3 in the candidate line (step S122). The CPU generates an emphasis map reflecting the determined weight setting (step S123), and superimposes the generated emphasis map on the original diagnostic image (step S124). The CPU then stores, into the storage unit 161, the ultrasound image having the estimated range of the puncture needle 3 emphasized, and ends the puncture needle detection emphasizing process.

As described above, the ultrasound diagnosis apparatus U of this embodiment is an ultrasound diagnosis apparatus that generates an ultrasound image of the inside of a test object based on ultrasound signals reflected and received from the inside of the test object. The ultrasound diagnosis apparatus U includes: the detection map generating unit 162 that extracts candidate points in the needle position range corresponding to the position of the puncture needle 3 inserted into the test object; the puncture needle identifying unit 163 that determines the candidate line including the needle position on range from the ultrasound image based on the extracted candidate points; and the emphasizing unit 164 that determines an estimated needle position range on the candidate line based on the value indicating the aggregation state related to the distribution of candidate points on the candidate line, and performs a process for emphasizing the estimated range in the ultrasound image.

As the needle position range corresponding to the position of the puncture needle 3 is determined to be the entire range depending on the aggregation state related to the distribution of candidate points, the possibility that a completely wrong position is detected as the edge position due to noise can be lowered. Accordingly, through a simple process, the position of the puncture needle 3 can be appropriately determined so as not to cause any serious problem to the user.

The value indicating the aggregation state includes the number of the candidate points existing on the candidate line, and the estimated range is determined in accordance with the number of the candidate points. Since the number of candidate points normally increases with the length of the puncture needle 3, the estimated range corresponding to the length of the puncture needle 3 can be readily set. Accordingly, the possibility that the estimated range will be longer or shorter than the actual length of the puncture needle 3 in a diagnostic image can be lowered.

Further, the value indicating the aggregation state includes the variance of the positions of the candidate points existing on the candidate line, and the estimated range is determined in accordance with the variance. Accordingly, even in a diagnostic image where the density of candidate points varies due to the thickness of the puncture needle 3, an estimated range with an appropriate length can be set.

The emphasizing unit 164 performs weighting on the result of estimation of an estimated range at the respective pixel positions in the estimated range based on the value indicating the aggregation state, and performs a process to emphasize the inside of the estimated range with the degree of emphasis corresponding to the weighting. With this, the influence of sporadic noise or a structure located at a distance from the puncture needle 3 is reduced, and it is made clear that the puncture needle 3 does not necessarily exist in the vicinities of both ends of the estimated range. Accordingly, the possibility that a serious problem will be caused to the user can be lowered.

Further, the value indicating the aggregation state includes the value that is set as the center position among the candidate points existing on the candidate line, and the emphasizing unit 164 performs weighting using a predetermined filter so that the weight becomes smaller at least on one side of the center position.

Accordingly, the user can readily obtain the information indicating how accurate the estimate is, particularly in the vicinity of an end of the estimated position of the puncture needle 3. Thus, it is possible to lower the possibility that a problem will be caused by the user wrongly recognizing the position of the edge of the puncture needle 3.

Furthermore, as the variance is set on either side of the center position, different ranges can be set for the side on which the puncture needle 3 extends from outside the diagnostic image, and for the side on which scattering becomes relatively larger toward the edge of the puncture needle 3. Accordingly, the user can visually recognize the emphasized display with greater ease as the accuracy of the estimated range becomes higher.

Further, as the set center position is the weighted average position among the candidate points existing on the candidate line, the portion where a large number of candidate points on the candidate line are detected and the possibility of existence of the puncture needle 3 is high is covered without fail. At the same time the weight is gradually reduced toward the end portion, with the center position serving as the reference position. Accordingly, the possibility that the weight becomes smaller in an unnatural position can be lowered even if a simple window function is used.

Furthermore, the weighted average position is the position calculated in accordance with the distribution of candidate points existing on the candidate line weighted with the values corresponding to the intensities of the ultrasound signals at the candidate points. Accordingly, the weighted average position can be calculated, with priority being put on the data of the detected candidate points of the puncture needle 3 with higher accuracy. Thus, the center position is not easily set in an unnatural position, and an appropriately estimated range is likely to be set.

Meanwhile, the detection map generating unit 162 extracts candidate points based on the distribution of ultrasound signals in the incident direction of ultrasound waves that enter the test object. Accordingly, the candidate points on the puncture needle 3 can be more accurately extracted with the use of a difference in luminance between the downstream side of the puncture needle 3 on which propagation of ultrasound waves is hindered by the puncture needle 3, and the upstream side of the puncture needle 3.

Furthermore, the puncture needle identifying unit 163 determines a straight candidate line having neither end determined in an ultrasound image. Accordingly, the candidate line in conformity with the shape of the puncture needle 3 can be readily and accurately identified through Hough transform or the like.

It should be noted that the present invention is not limited to the above described embodiment, and various modifications may be made.

For example, in the above described embodiment, a technique of more accurately detecting the position of the puncture needle 3 by using the shadow (acoustic shadow) formed by the puncture needle 3. However, some other method, such as conventional selection based on luminance values, may be used in extracting candidate points.

Further, the candidate points selected on a pixel basis in the above described embodiment may be set not on a pixel basis but on some other basis (for each set of pixels, for example) depending on purposes such as for decreasing high-frequency noise.

Further, in the above described embodiment, the predetermined parameters include the weighted average position among candidate points, the number of the candidate points, and the variance among the positions of the candidate points. However, the predetermined parameters are not limited to this combination of values. Further, the predetermined parameters may not include a value indicating an aggregation state, but may include the value indicating the center position in the array, for example.

Further, in the above described embodiment, the ultrasound diagnosis apparatus U has been described as a combination of the ultrasound diagnosis apparatus main frame 1 and the ultrasound probe 2. However, the ultrasound diagnosis apparatus U may be formed only with the ultrasound diagnosis apparatus main frame 1, and the ultrasound diagnosis apparatus main frame 1 may be used in conjunction with an external ultrasound probe 2 or the like.

The other specific aspects such as the structures, the processes, and the procedures described in the above embodiment may be modified as appropriate, without departing from the scope of the invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An ultrasound diagnosis apparatus comprising:
at least one hardware processor which is configured to:
generate an ultrasound image of an inside of a test object based on ultrasound signals reflected and received from the inside of the test object;
extract a plurality of candidate detection regions in a needle position range corresponding to a position of a puncture needle inserted into the test object;
determine a needle identification range including the needle position range from the ultrasound image based on the extracted candidate detection regions;
determine an estimated range of the needle position range in the needle identification range based on a value indicating an aggregation state related to a distribution of the candidate detection regions in the needle identification range; and
perform a process for emphasizing the estimated range in the ultrasound image,
wherein the value indicating the aggregation state includes a value indicating a center position in the aggregation of the candidate detection regions existing in the needle identification range, and the at least one hardware processor performs the process for emphasizing the estimated range by performing weighting, using a predetermined window function to reduce the weighting at least on one side of the center position, and wherein the at least one hardware processor is further configured to calculate a density of candidate points in each of a plurality of ranges of a predetermined size within the estimated range, to determine whether a ratio of (i) the calculated density of candidate points in each of said plurality of ranges to (ii) the calculated density in a range among said plurality of ranges that includes the center position, is equal to or higher than a predetermined ratio, and to perform the process for emphasizing the estimated range such that a degree of emphasis corresponding to the weighting is not lowered in each of said ranges for which it is determined that the ratio of the calculated density to the density in the range including the center position is equal to or higher than the predetermined ratio.

2. The ultrasound diagnosis apparatus according to claim 1, wherein the value indicating the aggregation state includes the number of the candidate detection regions existing in the needle identification range, and the estimated range is determined in accordance with the number of the candidate detection regions.

3. The ultrasound diagnosis apparatus according to claim 1, wherein the value indicating the aggregation state includes variance among positions of the respective candidate detection regions in an aggregation of the candidate detection regions existing in the needle identification range, and the estimated range is determined in accordance with the variance.

4. The ultrasound diagnosis apparatus according to claim 1, wherein the value indicating the aggregation state includes variance among positions of the respective candidate detection regions in an aggregation of the candidate detection regions existing in the needle identification range, the estimated range is determined in accordance with the variance, and the variance is determined independently on either side of the center position.

5. The ultrasound diagnosis apparatus according to claim 1, wherein the center position is a weighted average position in the aggregation of the candidate detection regions existing in the needle identification range.

6. The ultrasound diagnosis apparatus according to claim 5, wherein the weighted average position is a position calculated in accordance with a distribution of the candidate detection regions weighted with values corresponding to intensities of the ultrasound signals in the candidate detection regions existing in the needle identification range.

7. The ultrasound diagnosis apparatus according to claim 1, wherein the at least one hardware processor extracts the candidate detection regions based on a distribution of the ultrasound signals in an incident direction of ultrasound waves entering the test object.

8. The ultrasound diagnosis apparatus according to claim 1, wherein the at least one hardware processor sets the needle identification range in the form of a straight line which extends across an entirety of the ultrasound image such that end points of the straight line are not defined in the ultrasound image.

* * * * *